Figure 1:
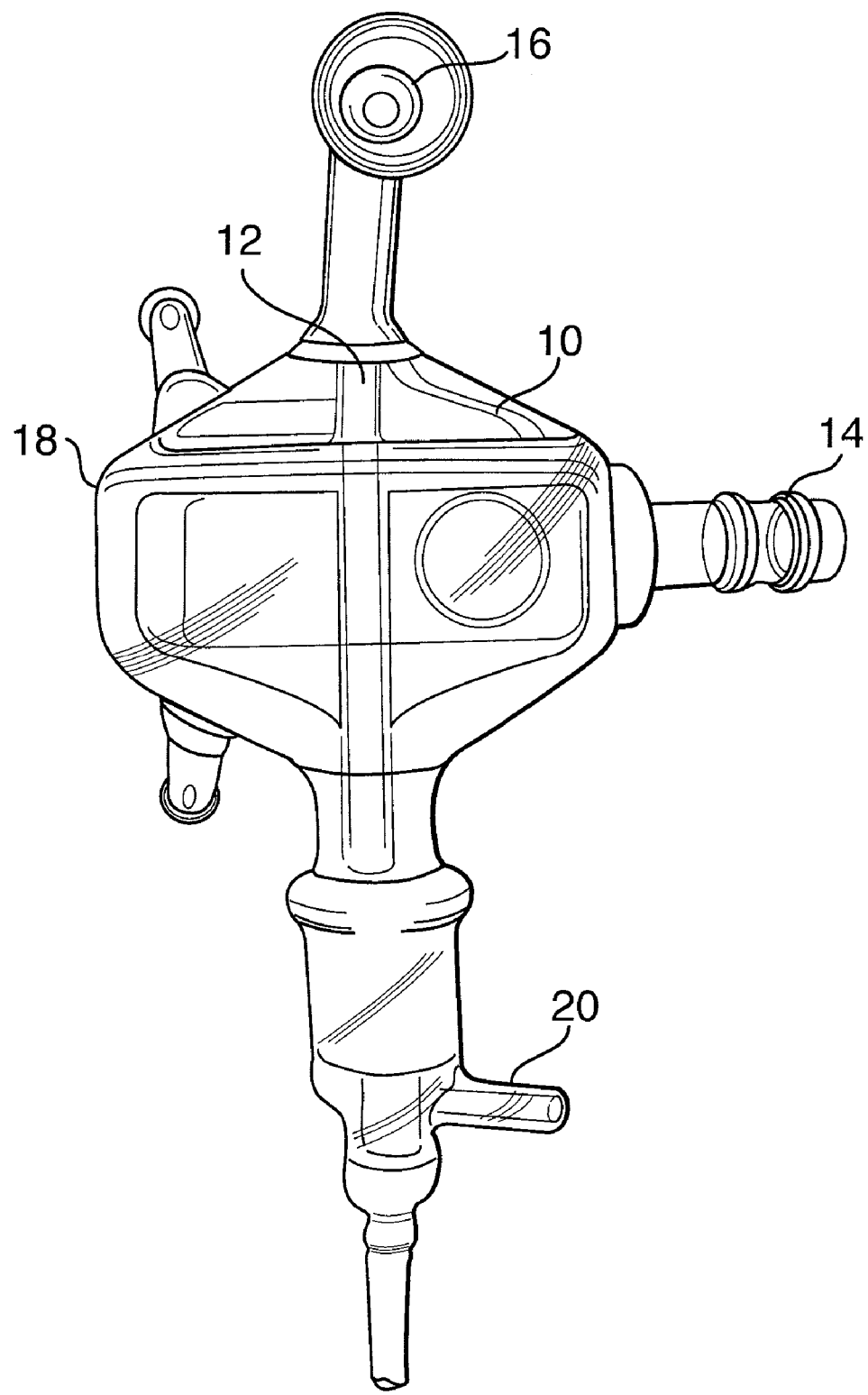

US007829872B2

(12) United States Patent
Sturgeon et al.

(10) Patent No.: US 7,829,872 B2
(45) Date of Patent: Nov. 9, 2010

(54) UV REACTIVE SPRAY CHAMBER FOR ENHANCED SAMPLE INTRODUCTION EFFICIENCY

(75) Inventors: Ralph Edward Sturgeon, Orleans (CA); Zoltan Mester, Orleans (CA); Xuming Guo, Ottawa (CA)

(73) Assignee: National Research Council of Canada, Ottawa, Ontario (CA)

( * ) Notice: Subject to any disclaimer, the term of this patent is extended or adjusted under 35 U.S.C. 154(b) by 732 days.

(21) Appl. No.: 11/721,313

(22) PCT Filed: Dec. 12, 2005

(86) PCT No.: PCT/CA2005/001870

§ 371 (c)(1),
(2), (4) Date: Jun. 8, 2007

(87) PCT Pub. No.: WO2006/063438

PCT Pub. Date: Jun. 22, 2006

(65) Prior Publication Data

US 2009/0236544 A1 Sep. 24, 2009

Related U.S. Application Data

(60) Provisional application No. 60/635,447, filed on Dec. 14, 2004.

(51) Int. Cl.
*G21G 4/00* (2006.01)

(52) U.S. Cl. ................................ 250/493.1; 250/504 R

(58) Field of Classification Search ....................... None
See application file for complete search history.

(56) References Cited

U.S. PATENT DOCUMENTS

| | | | | |
|---|---|---|---|---|
| 4,810,654 | A | | 3/1989 | Tao |
| 5,051,557 | A | * | 9/1991 | Satzger .................. 219/121.52 |
| 5,068,534 | A | * | 11/1991 | Bradshaw et al. ........... 250/288 |
| 5,246,782 | A | * | 9/1993 | Kennedy et al. ............ 428/421 |
| 5,409,777 | A | * | 4/1995 | Kennedy et al. ......... 428/411.1 |
| 5,495,107 | A | * | 2/1996 | Hu et al. ..................... 250/281 |
| 5,730,922 | A | * | 3/1998 | Babb et al. .................. 264/258 |
| 5,939,648 | A | | 8/1999 | Phan |

(Continued)

FOREIGN PATENT DOCUMENTS

CA 2437489 A1 2/2004

OTHER PUBLICATIONS

Guo et al. "UV Vapour Generation for Determination of Selenium by Heated Quartz Tube Atomic Absorption Spectrometry"; Analytical Chemistry; vol. 75, No. 9, May 1, 2003; pp. 2092-2099.*

(Continued)

*Primary Examiner*—Bernard E Souw
*Assistant Examiner*—Andrew Smyth
(74) *Attorney, Agent, or Firm*—Marks & Clerk; Richard J. Mitchell

(57) ABSTRACT

An analyte for atomic spectrometry detection is prepared by introducing an aerosol of the analyte into a chamber, and irradiating the aerosol with ultraviolet light in the presence of a low molecular weight organic acid or other suitable photo-activatable ligand donor species to create vapor containing the analyte. The vapor containing the analyte is extracted from the chamber and used for atomic spectrometry detection.

25 Claims, 2 Drawing Sheets

U.S. PATENT DOCUMENTS

| | | | |
|---|---|---|---|
| 6,288,390 B1* | 9/2001 | Siuzdak et al. | 250/288 |
| 6,528,016 B1* | 3/2003 | Kohler et al. | 422/28 |
| 6,746,647 B2* | 6/2004 | Kohler et al. | 422/28 |
| 6,972,056 B1* | 12/2005 | Delzeit et al. | 134/1 |
| 7,087,692 B2* | 8/2006 | Koshti et al. | 526/217 |
| 7,115,720 B2* | 10/2006 | Fritzberg | 534/14 |
| 7,123,361 B1* | 10/2006 | Doughty | 356/316 |
| 2002/0081228 A1* | 6/2002 | Hui et al. | 422/3 |
| 2003/0052278 A1* | 3/2003 | Duarte | 250/438 |
| 2003/0063997 A1* | 4/2003 | Fryer et al. | 422/3 |
| 2003/0156977 A1* | 8/2003 | Kohler et al. | 422/28 |
| 2003/0230712 A1 | 12/2003 | McLaughlin et al. | |
| 2004/0079881 A1* | 4/2004 | Fischer et al. | 250/288 |
| 2004/0096393 A1* | 5/2004 | Fritzberg | 424/1.11 |
| 2004/0101498 A1* | 5/2004 | Koshti et al. | 424/59 |
| 2005/0163648 A1* | 7/2005 | Liang | 422/1 |
| 2005/0269254 A1* | 12/2005 | Roitman | 210/252 |

OTHER PUBLICATIONS

Guo et al., "Vapour Generation by UV Irradiation for Sample Introduction with Atomic Spectrometry"; Analytical Chemistry, vol. 76, No. 8, Apr. 15, 2004, pp. 2401-2405.*

X. Guo, R.E. Sturgeon, Z. Mester, G.J. Gardner, "UV Vapour Generation for Determination of Selenium by Heated Quartz Tube Atomic Absorption spectrometry", Analytical Chemistry; vol. 75, No. 9, May 1, 2003; pp. 2092-2099.

X. Guo, R.E. Sturgeon, Z. Mesterm G.J. Gardner; :Vapour Generation by UV Irradiation for Sample Introduction with Atomic Spectrometry, Analytical Chemistry, vol. 76, No. 8, Apr. 15, 2004, pp. 2401-2405.

R. McLaughlin and I. Brindle; "A New Sample Introduction System for Atopmic Spectrometry Combining Vapour Generation and Nebulization Capacities", Journal of Analytical Atomic Spectrometry, vol. 17, No. 11, pp. 1540-1548; 15 Oc. 2002.

"Ultrafast Chemical Separations" (1993); Commission on Physical Sciences, Mathematics and Applications (CPSMA), National Academies Press, (Retrieved on Mar. 7, 2006).

R.E. Sturgeon, Z. Mester; "Analytical Applications of Volatile Metal Derivatives", Applied Spectroscopy; vol. 56/8 p. 202-213.

"Determination of transition and rare earth elements in seawater by flow injection inductively coupled plasma time-of-flight mass spectrometry", S.N. Willie, R.E. Sturgeon, Inst, for National Measurement Standards, National Research Council of Canada, Ottawa Ontario Canada, Spectrochimica Acta Part B (2001) 1707-1716.

* cited by examiner

UV REACTIVE SPRAY CHAMBER FOR ENHANCED SAMPLE INTRODUCTION EFFICIENCY

CROSS REFERENCE TO RELATED APPLICATION

This application claims the benefit under 35 USC 119(e) of U.S. provisional application Ser. No. 60/635,447, filed Dec. 14, 2004.

FIELD OF INVENTION

This application relates to an apparatus and a method for generating a gaseous form of an element from a liquid sample containing the element.

BACKGROUND OF THE INVENTION

Atomic spectrometry detection frequently requires the ready availability of a liquid sample. Conventional sample introduction techniques for atomic spectrometry detection rely predominantly on pneumatic nebulization of liquids.

There are several techniques in current use for vapor generation, but this is classically accomplished using chemical derivatization reactions which are conducted in separate modules and frequently independent of the sample nebulization process. The most popular of these techniques is the so called hydride generation approach, which relies on the reductive hydridization of a small number of elements by the action of an aqueous solution of sodium tetrahydroborate. This approach, as well as others relating to halide generation and aqueous alkylation reactions for generation of volatile slightly water soluble forms of metals is discussed in R. E. Sturgeon and Z. Mester, Analytical Applications of Volatile Metal Derivatives, *Appl. Spectrosc.* 56 202A-213A (2002).

These metal vapour generation protocols are limited in scope to a handful of elements and are themselves difficult to implement, frequently requiring separate gas-liquid separators and excluding all other elements not amenable to the derivatization reaction.

Enhancement of sample introduction efficiency is currently being pursued by many practitioners of atomic spectrometry. Current activity includes the design of improved nebulizers and spray chambers, frequently operating at low sample uptake and ultimately relying on their integration or complete elimination of the latter so as to achieve 100% efficiency or utilizing chemical vapor generation (CVG) to convert the analytes of interest to volatile species, thereby achieving similar results. CVG is undergoing a resurgence of interest in the past decade following the report of a volatile species of copper generated during merging of an acidified solution of the analyte with that of sodium tetrahydroborate reductant. Subsequently, a number of transition and noble metals have been detected based on similar reactions, but typically under conditions facilitating rapid separation of the relatively unstable product species from the liquid phase. This requirement is most easily met when the sample and reductant solutions are merged at the end of a concentric or cross-flow nebulizer, the resultant aerosol providing a unique atmosphere for rapid release of the volatile product from a large surface-to-volume phase into an inert transport gas.

A simplified and potentially "cleaner" arrangement for vapor generation can be realized with the use of ultraviolet irradiation. See, for example, X. Guo, R. E. Sturgeon, Z. Mester and G. J. Gardner, UV Vapor Generation for Determination of Se by Heated Quartz Tube AAS, *Anal. Chem.* 75 2092-2099 (2003). Although UV has been widely deployed to assist with oxidative sample preparation, its application as a tool for alkylation of a number of metals has only recently emerged. Radical induced reactions in irradiated solutions of low molecular weight organic acids provide small ligands capable of reducing, hydrogenating and/or alkylating a number of elements to yield volatile products. X. M. Guo, R. E. Sturgeon, Z. Mester and G. J. Gardner, *Anal. Chem.,* 2004, 76, 2401-2405.

To date, the process of photoalkylation for analytical purposes (enhanced detection capability for metals, semi-metals or non-metals) has been achieved using either one of two approaches: irradiation of sample in a batch reactor containing the analyte element of interest and the LMW acid which is connected to analytical instrumentation used for element detection via a gas transport line; or by irradiation of a continuous flowing stream of sample containing the analyte element of interest and the LMW acid which is directed to a gas-liquid separator for phase separation and transport of a carrier gas containing the generated analyte to the detection system. These techniques are not, however, suitable for efficient sample preparation for atomic spectrometry equipment.

SUMMARY OF THE INVENTION

According to a first aspect of the invention there is provided a method preparing an analyte for atomic spectrometry detection comprising introducing an aerosol of the analyte into a chamber; irradiating the aerosol with ultraviolet light in the presence of a low molecular weight organic acid or other suitable photoactivatable ligand donor species to create a reduced, hydrogenated and/or alkylated and/or elemental vapor containing the analyte; and extracting the vapor from the chamber for use in atomic spectrometry.

The analyte can typically be metallic or metalloid elements, and any non metallic elements from main groups V, VI and VII of the periodic table that form volatile adducts, such as transition metals, heavy metals, semi-metals, halides and precious metals.

The low molecular weight organic acid or other alkyl donor species should provide a concentration of 1000 times the molar level of the analyte, preferably from 0.001 to 10 M, and more preferably from 0.01 to 10M.

Ultraviolet light is suitable for the method. If the wavelength is too high, above about 400 nm, no reaction is observed. If the wavelength is to low (too high photon energy), complete decomposition of the organic acid and volatile metal product may occur. Typically, ultraviolet includes wavelengths below about 360 nm.

The source of ultraviolet light can be a 254 nm mercury discharge lamp. The liquid sample is preferably de-aerated.

A low molecular weight (LMW) organic acid is herein defined as an organic acid of molecular weight less than 100 Daltons.

During the irradiation process, volatile reduced, hydrogenated and/or alkylated element compounds are formed and released from the sample in the flow of carrier gas or as a result of their inherent vapour pressure and low solubility in the solution. Currently, volatile species of As, Bi, Sb, Se, Sn, Pb, Cd, Te, Hg, Ni, Co, Cu, Fe, Ag, Au, Rh, Pd, Pt, I and S have been generated in this manner and specifically monitored and detected. It appears that this approach may encompass many elements, such as those in Groups IIIA, IVA, VA, VIA, VIIA and IIIB, IVB, VB, VIB and VIII of the Periodic Table. The inventors have not yet identified a complete list of elements that suitable, but such elements can be determined by routine experimentation. For example, it is believed that Br and Cl would work well.

According to another aspect of the invention there is provided an apparatus for preparing an analyte for atomic spectrometry detection, comprising a spray chamber; an aerosol injector for introducing the analyte into the spray chamber as an aerosol; a source of low molecular weight organic acid or other suitable photoactivatable ligan donor species; an ultraviolet radiation source for irradiating the analyte in the chamber in the presence of the low molecular weight organic acid or other suitable photoactivatable alkyl donor species to create a reduced, hydrogenated and/or alkylated and/or elemental vapor containing the analyte; and an outlet port for supplying the vapor containing the analyte to an atomic spectrometry detector.

The invention takes advantage of the process of photoalkylation by UV light in the presence of added low molecular weight organic acids to efficiently prepare a gas phase volatile form of a trace element to enhance the transfer of this form of the element to a cell used for its subsequent detection by atomic emission, absorption, fluorescence or mass spectrometry.

BRIEF DESCRIPTION OF THE DRAWINGS

FIG. 1 illustrates one embodiment of the UV Reactive Spray Chamber.

FIG. 2 shows the effect of ultraviolet field on response from $^{78}$Se, $^{127}$I and $^{202}$Hg during steady-state introduction of a 5 ng/ml multielement solution containing 5% propionic acid. Vertical bars indicate onset and termination of UV discharge.

FIG. 3 shows the effect of ultraviolet field on response from $^{78}$Se, $^{127}$I and $^{202}$Hg during steady-state introduction of a 5 ng/ml multielement solution containing 5% acetic acid. Vertical bars indicate onset and termination of UV discharge.

DETAILED DESCRIPTION OF THE PREFERRED EMBODIMENTS

FIG. 1 illustrates one embodiment of the present invention, which is a modified commercial cyclonic spray chamber 10, typically used for pneumatic liquid sample introduction. It has a small pen lamp low pressure mercury discharge lamp 12 inserted along the central axis of the spray chamber in such a manner as to not impede the normal operation of the spray chamber, including sample introduction, and waste removal by a waste drain 20.

Normally, the sample is introduced via a nebulizer, which is mounted in port 14 to result in the creation of a fine aerosol mist, 1-5% of which travels to the outlet port 16. This is connected to the remainder of the detection system forming part of the atomic spectrometry equipment (not shown).

The aerosol can be created in a number of ways, such as pneumatic nebulization, hydraulic high pressure, thermospray, electrospray, ultrasonic, concentric and cross-flow liquid introduction systems.

When used in the preferred manner, a suitable concentration of LMW organic acid (in the range 0.01 to 10 M) added to the sample before it is pumped into the spray chamber via the nebulizer port 14, whereupon it is exposed to ultraviolet irradiation from the mercury source 12. In such circumstances, the rapid reduction, hydrogenation and/or alkylation of many elements in the solution sample occurs and their gas-liquid phase separation from the solution is facilitated by the formation of the aerosol as well as aided by the normal nebulizer gas flow. The result is an enhanced efficiency of transport of the analyte element (up to 100%) to the detection system.

The embodiment of the UV reactive spray chamber as illustrated in FIG. 1 provides for one means of achieving the desired production of volatile element species for enhanced sample introduction efficiency. Alternative forms may include physical variations of the spray chamber to address all current commercial versions, such as the Scott, cyclone and conical and those based on desolvation systems as well as include all means of pneumatic and self-aspirating sample introduction systems, including those designed for integrated approaches to sample introduction which take advantage of pneumatic nebulization and hydride generation. See, R. L. J. McLaughlin and I. D. Brindle, A new sample introduction system for atomic spectrometry combining vapour generation and nebulization capacities, J. *Anal. At. Spectrom.,* 17, 1540-1548 (2002), the contents of which are herein incorporated by reference.

The arrangement for the UV source is also highly variable and can be as illustrated in FIG. 1 or physically envelope partially or completely the chamber walls containing the nebulized aerosol.

As an example, the current water cooling jacket 18 on the cyclonic spray chamber illustrated in FIG. 1 could form the envelope of a low pressure mercury discharge source, made more efficient by application of a reflecting mirror to the exterior surface. Similarly, the source of UV energy can vary in intensity for optimum application and the operating wavelength should be less than 400 nm, although the optimum is the 253.7 nm Hg resonance line.

EXAMPLE

A 50 ml internal volume water jacketed Twister cyclonic spray chamber (Glass Expansion, Victoria, Australia) was used. The standard waste removal line was modified to accommodate the mounting of a 6 W UVC mercury pen lamp (Analamp, Claremont, Calif., model 81-1057-51λmax 253.7 nm) having a 50 mm lighted length and 5 mm o.d.

This was achieved by removing the handle and mounting the lamp barrel in the ground glass fitting of the waste line using epoxy resin, as illustrated in FIG. 1. In operation, the lamp thus extended along the vertical central axis of the spray chamber and did not impede the normal pneumatic operation of the device. The spray chamber was fitted with a Conikal concentric glass nebulizer (Glass Expansion, model 70115) and fed with sample via a peristaltic pump at a nominal flow rate of 1 ml/min.

The nebulizer/spray chamber was mounted on the end of the torch with a socket attachment and supported an ICP in an Optimass 8000 TOF-MS instrument (GBC Scientific Equipment Pty. Ltd., Australia). Typical operating conditions for the ICP-TOF-MS instrument are summarized in S. N. Willie and R. E. Sturgeon, *Spectrochim. Acta, Part B,* 2001, 56, 1701-1716, the contents of which are incorporated by reference.

Formic, acetic and propionic low molecular weight organic (LMW) acids were obtained from Anachemia and BDH and used without purification. Reverse osmosis water was further purified by deionization in a mixed-bed ion-exchange system (NanoPure, model D4744, (Barnstead/Thermoline, Dubuque, Iowa) and nitric and hydrochloric acids were purified in-house from commercial stocks by sub-boiling distillation. Five ng/ml multielement solutions containing Ag, As, Ba, Bi, Cd, Cu, Pb, Hg, I, Sb, In, Ni, Sn and Se were prepared in high purity water containing either 1% (v/v) $HNO_3$ or nominally 1 and 5% (v/v) LMW acids.

The ICP-TOF-MS was first optimized for response by introducing an approximately 1 ml/min 10 ng/ml solution of Ho in 0.5% (v/v) $HNO_3$. Steady-state response from a multielement solution containing $HNO_3$ and from each of the three solutions containing the LMW acids was measured with and without the mercury discharge lamp on. In each case, the average response from 3 replicate 5 s integration periods was used. The temporal characteristics of the signals were also monitored using 1 s continuous integration readings.

Sensitivities for all elements in the presence of the LMW acids were significantly lower than achieved with a nitric acid solution (5-50-fold), in part because instrument performance was optimized using a nitric acid solution and the changes in density, viscosity, wetting characteristics and decomposition products associated with the LMW acid solutions created non-optimum aerosol characteristics. It is possible that the benefits accruing from the use of the UV field, described below, could be enhanced if sample introduction had first been optimized for each solution.

Figure 2:
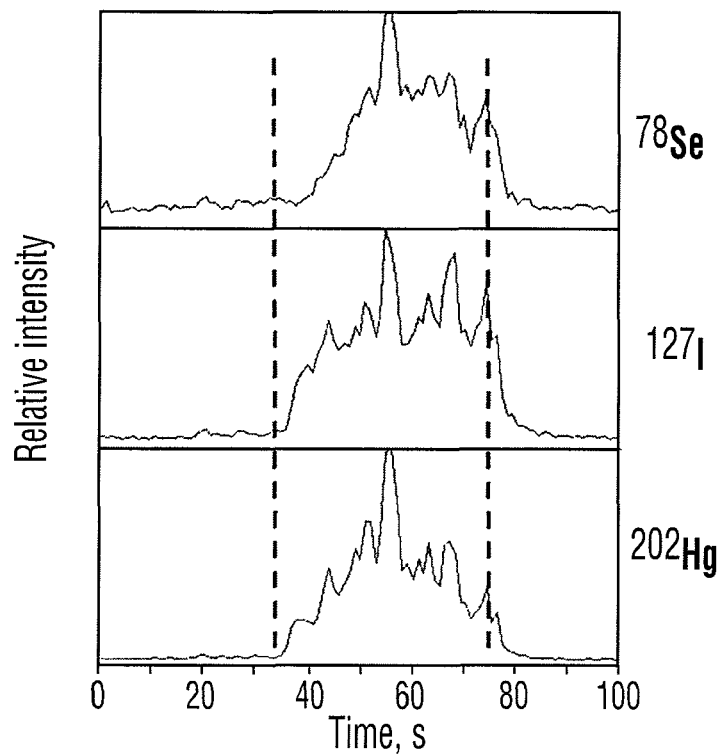
Figure 3:
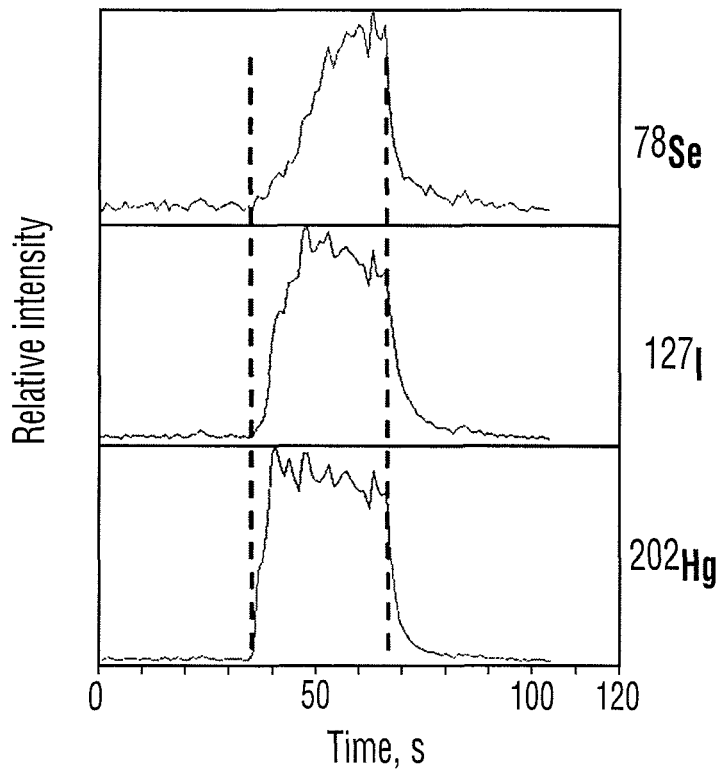

FIGS. 2 and 3 illustrate the time dependence of the evolution of the enhanced signals for $^{78}Se$, $^{127}I$ and $^{202}Hg$ when the mercury lamp is powered, exposing the introduced aerosol to UV photolysis. Pronounced changes in the intensities of the signals for many elements were noted; these are summarized in Table 1. The suite of elements listed is not meant to be comprehensive.

Most notable are the enhanced signals for elements such as Se, Bi, I, Hg and Pb in all LMW acids and Sb and Sn in formic and acetic acids. Barium was monitored as it is assumed to be unaffected by any alkylation reactions and changes in its intensity in the presence of the UV field likely reflect physical alterations in the measurement system. Evolution of carbon oxides as well as hydrogen and perhaps hydrocarbons may occur during photolytic oxidation of the LMW acids which will change the optimum sampling depth of the plasma and give rise to fluctuations in the baseline and sensitivity of the system. Thus, to some degree, the effects noted for Ba may be used to infer other physical changes in the detection system that occur over and above those associated with real enhancements in sample introduction efficiency for some elements. The same observation is evident with the introduction of analytes in 1% nitric acid. Table 1 shows that, with the exception of Hg, UV photolysis results in a nearly uniform 25% suppression in response for all elements. It may thus be inferred that evolution of molecular gases, such as nitrogen oxides, and/or the presence of the heated lamp post in the spray chamber, gives rise to an alteration in the aerosol distribution or composition, inducing a change in plasma chemistry/optimum sampling depth.

Photo-oxidation is a radical mediated reaction and response to the presence/absence of the UV field should be immediate. Alkylation of a number of elements may lead to production of reduced metal or halide and hydrides, methyl and ethyl analogues of the analyte in formic, acetic and propionic acids, respectively. The relatively slow rise and fall of the signals for these elements in response to the lamp being turned on and off is likely a consequence of the wetting of the internal walls of the spray chamber and the release of the volatile analyte species from the liquid phase. This is consistent with the increasingly longer time required to achieve steady-state response for Se, for example. As the LMW acid is changed from formic to acetic to propionic the "rise time" of the signal increases from 9 to 14 to 18 s. Earlier studies have shown that such radical reactions lead to alkyl substitution onto the metal, resulting in hydride, dimethyl- and diethyl-Se compounds which are expected to have correspondingly decreasing vapor pressures. Thus, a delay time, characteristic of sample wash-in and wash-out for a spray chamber, is evident in these experiments in response to powering the UV lamp on and off.

Mass 220 Da was also monitored in each system to reveal any changes in the background over time. The influence of the UV field was difficult to detect as the total counts acquired were relatively small at this mass. All effects were significantly smaller than noted for Ba.

Table 1 summarizes the relative enhancement factors attained in the various LMW acids in response to the presence of the UV field. Data highlighted in bold face indicate those elements for which an enhanced sensitivity is accorded to the presence of the UV field, the magnitude of the effect surpassing any signal changes noted for Ba and assigned to plasma effects accompanying photolysis reactions.

TABLE 1

Relative intensity enhancement factors in response to UV photoalkylation.

| | Low Molecular Weight Acid Concentration | | | | | | |
|---|---|---|---|---|---|---|---|
| | % formic | | % acetic | | % propionic | | |
| Element | 1 | 5 | 1 | 5 | 1 | 5 | 1 % nitric |
| Cu | 1.0 | 0.9 | 1.4 | 3.3 | 1.7 | 1.8 | .66 |
| Ag | 1.8 | 1.2 | 7.6 | 6.4 | 2.5 | 2.6 | .67 |
| Cd | 1.0 | 1.2 | 2.0 | 3.9 | 1.9 | 2.0 | .70 |
| As | 1.1 | 1.7 | 1.6 | 4.4 | 2.0 | 2.6 | .71 |
| Se | 2.8 | 16 | 19 | 29 | 5.6 | 6.3 | .78 |
| Ba | 1.0 | 1.1 | 1.5 | 3.6 | 1.8 | 1.7 | .72 |
| Sb | 1.0 | 9.3 | 2.9 | 4.6 | 2.0 | 2.3 | .75 |
| Hg | 18 | 17 | 5.1 | 16 | 17 | 17 | 1 |
| I | 2.2 | 3.1 | 12 | 38 | 12 | 16 | .84 |
| Bi | 0.9 | 4.2 | 43 | 18 | 3.3 | 9.7 | .77 |
| Pb | 1.0 | 2.0 | 7.0 | 5.9 | 2.5 | 3.1 | .78 |
| Ni | 1.1 | 1.7 | 1.6 | 2.9 | 1.6 | 1.7 | .67 |
| Sn | 1.0 | 5.6 | 3.2 | 5.2 | 2.1 | 2.1 | .69 |
| In | 1.0 | 0.9 | 1.5 | 3.9 | 1.9 | 1.9 | .69 |

*based on the relative intensity change in the signal in the presence/absence of the UV field. The table headings need to be re-aligned The combination of UV irradiation with pneumatic sample introduction of solutions containing LMW organic acids offers a simple and convenient approach by which the benefits of photoalkylation can be easily realized. The influence of the intensity of the UV field requires study as only a low power lamp was used for these experiments. Redesign of the spray chamber to create a full annular discharge, creating the ultraviolet light within the space currently used for the water jacket or use of a larger surface area Scott-type spray chamber may enhance efficiencies and minimize the "wash-in and wash-out" effects.

The invention claimed is:

1. A method preparing an analyte for atomic spectrometry detection comprising:
    introducing an aerosol of the analyte into a chamber;
    irradiating the aerosol with ultraviolet light in the presence of a low molecular weight organic acid or other suitable photoactivatable ligand donor species to create a reduced, hydrogenated and/or alkylated and/or elemental vapor containing the analyte; and
    extracting the vapor from the chamber for use in atomic spectrometry.

2. A method as claimed in claim 1, wherein the chamber is a spray chamber.

3. A method as claimed in claim 1, wherein the low molecular weight organic acid or other ligand donor species provides a concentration of 0.001 to 10 M.

4. A method as claimed in claim 1, wherein the aerosol is irradiated in the presence of a low molecular weight acid having a molecular weight <100 Da.

5. A method as claimed in claim 3, wherein the low molecular weight organic acid is formic acid, acetic acid, or propionic acid.

6. A method as claimed in claim 1, wherein the low molecular weight organic acid or other suitable photoactivatable ligand donor species is added to the analyte prior to formation of the aerosol.

7. A method as claimed in claim 6, wherein the aerosol is created with a nebulizer, and the analyte is supplied to the nebulizer mixed with said low molecular weight organic acid or other suitable photoactivatable ligand donor species.

8. A method as claimed in claim 1, wherein the other suitable photoactivatable ligand donor species comprises a suitable photoactivatable alkyl donor species.

9. A method as claimed in claim 1, wherein ultraviolet light is created by an annular discharge surrounding the chamber.

10. A method as claimed in claim 9, further comprising a reflecting surface to concentrate the light from said annular discharge into the chamber.

11. A method as claimed in claim 1, wherein the wavelength of the ultraviolet light is 253.7 nm.

12. A method as claimed in claim 1, wherein the analyte is an element selected from the group consisting of: Se, Bi, I, Hg and Pb and the ligand donor species is an LMW acid.

13. A method as claimed in claim 1, wherein the analyte is an element selected from the group consisting of: Sb and Sn and the ligand donor species is selected from the group consisting of: formic and acetic acids.

14. A method as claimed in claim 1, wherein the analyte is an element selected from the group consisting of: As, Bi, Sb, Se, Sn, Pb, Cd, Te, Hg, Ni, Co, Cu, Fe, Ag, Au, Rh, Pd, Pt, I and S.

15. A method as claimed in claim 1, wherein the analyte is selected from the group consisting of: metallic, metalloid, and halide elements.

16. A method as claimed in claim 1, wherein the analyte is selected from the group consisting of groups IIIA, IVA, VA, VIA, VIIA and IB, IIB, IIIB, IVB, VB, VIB and VIII of the Periodic Table.

17. An apparatus for preparing an analyte for atomic spectrometry detection, comprising:
    a spray chamber;
    an aerosol injector for introducing the analyte into the spray chamber as an aerosol;
    a source of low molecular weight organic acid or other suitable photoactivatable ligand donor species;
    an ultraviolet radiation source for irradiating the analyte in the chamber in the presence of the low molecular weight organic acid or other suitable photoactivatable ligand donor species to create a reduced, hydrogenated and/or alkylated and/or elemental vapor containing the analyte; and
    an outlet port for supplying the vapor containing the analyte to an atomic spectrometry detector.

18. An apparatus as claimed in claim 17, wherein said ultraviolet source is a mercury discharge lamp.

19. An apparatus as claimed in claim 17, wherein said ultraviolet source is an annular discharge chamber around said spray chamber.

20. An apparatus as claimed in claim 19, wherein said ultraviolet source includes a mirror reflector to concentrate ultraviolet light in said spray chamber.

21. An apparatus as claimed in claim 17, wherein said aerosol injector is a nebulizer provided in an inlet port for the spray chamber.

22. An apparatus as claimed in claim 17, wherein the aerosol injector is connected to a supply of the analyte mixed with the low molecular weight organic acid or other suitable photoactivatable ligand donor species to provide said source.

23. An apparatus as claimed in claim 17, wherein said outlet port is connected to atomic spectrometry detection equipment.

24. An apparatus as claimed in claim 17, wherein said source supplies a low molecular weight acid.

25. An apparatus as claimed in claim 24, wherein said source supplies formic acid, acetic acid, or propionic acid.

\* \* \* \* \*